United States Patent [19]

Lamberti et al.

[11] 4,003,925
[45] Jan. 18, 1977

[54] PURIFICATION OF SODIUM ISETHIONATE

[75] Inventors: Vincent Lamberti, Upper Saddle River; Beth Ann Di Lorenzo, Ridgewood, both of N.J.

[73] Assignee: Lever Brothers Company, New York, N.Y.

[22] Filed: June 12, 1975

[21] Appl. No.: 586,323

Related U.S. Application Data

[63] Continuation-in-part of Ser. No. 456,576, April 1, 1974, abandoned.

[52] U.S. Cl. .................. 260/513 R; 260/513 B; 260/637 R
[51] Int. Cl.² ........................................ C07C 143/10
[58] Field of Search ......... 260/513 R, 513 B, 637 R

[56] References Cited
UNITED STATES PATENTS 2,436,209  2/1948  Elgin .................. 260/637 R

OTHER PUBLICATIONS

Craig, et al, Tech. of Organic Chem., vol. III, Part I, pp. 301–304 (1956).
Rao et al, J. Appl. Chem., pp. 659–666 (1970).
Laddha et al, Ind. Eng. Chem., 40, 494 (1948).

Primary Examiner—James O. Thomas, Jr.
Assistant Examiner—Nicky Chan
Attorney, Agent, or Firm—James J. Farrell; Melvin H. Kurtz; Kenneth F. Dusyn

[57]  ABSTRACT

Glycol impurities in aqueous sodium isethionate solutions are readily removed by extraction with an aliphatic alcohol containing three to four carbon atoms. The use of the purified sodium isethionate results in improved processing of detergent bars containing coconut acyl isethionate prepared by direct esterification of sodium isethionate with coconut fatty acids.

6 Claims, No Drawings

PURIFICATION OF SODIUM ISETHIONATE

This application is a continuation-in-part application of copending Ser. No. 456,576, filed Apr. 1, 1974, now abandoned.

BACKGROUND OF THE INVENTION

This invention relates to an extraction process for removing glycol impurities from aqueous sodium isethionate solutions.

Sodium isethionate, which is manufactured by reaction of ethylene oxide with aqueous sodium bisulfite solution, is a key raw material in the manufacture of fatty acyl isethionate detergent compounds also known as Igepon A type surfactants. These compounds have achieved an important commercial status notably in the manufacture of detergent bars based on coconut acyl isethionate. One method of manufacturing sodium isethionate from ethylene oxide and sodium bisulfite is described in U.S. Pat. No. 2,810,747. A process for preparing coconut acyl isethionate is described in U.S. Pat. No. 3,320,292 (said patents incorporated herein by reference).

The manufacture of detergent bars based on coconut acyl isethionate involves a number of critical operating steps—one of the most important of which is a wet-mixing step during which the coconut acyl isethionate is blended at elevated temperature with water, stearic acid, soap and other minor ingredients. A description of the manufacture of such detergent bars is found in U.S. Pat. No. 2,894,912, incorporated herein by reference.

It is known that certain impurities in the sodium isethionate utilized for coconut acyl isethionate production can have a profound effect on the quality of the acyl isethionate produced. For example, the presence of sulfite in the sodium isethionate affects the odor quality of the detergent bars. Avoidance of such odor problems is the subject of U.S. Pat. No. 3,094,555 issued June 18, 1963 to the instant assignee (incorporated herein by reference).

It has now been found that the ethylene glycol content of the sodium isethionate is an important factor with respect to the processability of coconut acyl isethionate prepared from such sodium isethionate. In order to provide a product which is free from gritty or particulate matter, described as "sandy" by those in the art, it has been found that, among other conditions, the consistency of the batch during wet-mixing should be dough-like and plastic. The plastic mass undergoes a maximum of shearing and mixing in the sigma blade type mixers currently used in the manufacture of such detergent bars. If the batch, on the other hand, is liquid or "soupy" in appearance, shearing action and mixing is minimal or insufficient and leads to a notable increase in "sandy" bar production which has reduced consumer appeal and is generally commercial unacceptable, thereby requiring reworking—an expensive undertaking. Thus if the ethylene glycol content of the sodium isethionate solution is greater than about 1% by weight relative to the amount of sodium isethionate solute in the solution, the wet-mixing step in the process of U.S. Pat. No. 2,894,912 when utilizing the coconut acyl isethionate of U.S. Pat. No. 3,320,292 is adversely affected in that the batch tends to become "soupy" thereby leading to increased "sandy" bar production.

While some manufactures of sodium isethionate have been able to control the level of ethylene glycol content in their sodium isethionate production to an acceptably low level (e.g. about ≤ 0.9% by weight based on the amount of sodium isethionate solute in solution), a number of manufacturers, because of equipment limitations and/or other reasons, frequently produce sodium isethionate solution well beyond this specification making it unsuitable for coconut acyl isethionate detergent bar production.

In the current era of recurring raw material shortages, especially for petrochemically-derived materials such as sodium isethionate, it has become imperative to be able to utilize all available sodium isethionate produced, whether within specification or not. While off-quality materials can often be blended with better quality product, some batches of product are so far off specification with respect to glycol content that the blending operation requires too long a period of time and leaves the sodium isethionate customer facing a shortage of an essential ingredient in his respective manufacturing process.

If the sodium isethionate solution, prepared as heretofore described, is first evaporated to dryness to form a substantially dry powder, the ethylene glycol impurity which remains in this powder can be removed readily be standard extraction using an appropriate solvent such as, for example, acetone. However, it is preferred for handling purposes to receive the sodium isethionate in the form of an aqueous solution containing about 50–60% by weight sodium isethionate dissolved therein. Such a solution at normal temperatures has no undissolved sodium isethionate, is generally clear and readily pumpable. Further, since a majo part of coconut acyl isethionate is now made by a direct reaction process from coconut fatty acids and sodium isethionate involving elimination of water (as described in U.S. Pat. No. 3,320,292), it is uneconomical in terms of energy consumption to predry the sodium isethionate, (which is hygroscopic in anhydrous form), in order to ship it and then process of a water forming reaction. Instead, it is preferred to concentrate the aqueous isethionate solution containing 50–60% by weight of dissolved sodium isethionate solute content to a higher solute content, e.g. about 73%, just prior to charging into the reactor for conversion into coconut acyl isethionate. This concentration step is performed at a sufficiently high temperature to maintain a homogeneous solution.

Accordingly, the development of efficient methods for eliminating or lowering the level of the ethylene glycol impurity in commercial sodium isethionate solutions has become an important objective for those concerned with the utilization of coconut acyl isethionate in detergent bars.

DISCUSSION OF THE PRIOR ART

The extraction of ethylene glycol from various media has been studied by a number of investigators. A pertinent study is that of Laddha and Smith, Ind. Eng. Chem. 40, 494 (1948) who investigated the extraction of ethylene glycol from water with n-amyl alcohol and N-hexyl alcohol. These studies showed that both alcohols were relatively poor extractive solvents for removing ethylene glycol from aqueous solutions.

Another study of "Ternary Liquid Equilibria" has been performed by M.R. Rao, et al, J. Appl. Chem., 7, December 1957, pages 650 to 666. This study involves extraction of various components, including ethylene glycol at relatively high concentrations, in ternary systems.

The principles of extraction and the various types of apparatus utilized in extraction are well known in the art. A detailed review of the subject is found in the treatise edited by Arnold Weissberger, entitled "Technique of Organic Chemistry", Volume III, Chapter IV, Interscience Publishers, Inc., 1950 (incorporated herein by reference).

SUMMARY OF THE INVENTION

This invention is concerned with a two-phase extraction process for removing low concentrations of ethylene glycol which may be present as an impurity in commercial aqueous solutions of sodium isethionate.

It is an object of this invention to provide an economical and effective method of removing or lowering the ethylene glycol impurity in aqueous sodium isethionate solutions. The ethylene glycol content is decreased by a method comprising the steps of:

i. contacting an aqueous sodium isethionate solution having dissolved therein at least about 40% by weight of sodium isethionate and up to about 3% by weight of dissolved ethylene glycol impurity with an organic solvent selected from the group consisting of n-propanol, isopropanol, 2-butanol, isobutanol, n-butanol, t-butanol and mixtures thereof whereby a solvent phase and an aqueous phase are formed, and ii. removing the solvent phase containing the extracted ethylene glycol.

It is a further object of this invention to achieve the removal of the ethylene glycol impurity from aqueous sodium isethionate solutions without introducing into the product any new inorganic or organic materials which, if not subsequently removably, might have an adverse effect on the ultimate quality and use properties of detergent bars derived therefrom.

These and other objects of the invention which will become evident are achieved by a two-phase extraction process utilizing the above-mentioned aliphatic alcohols and, in particular, isopropanol, as the extractive solvent.

DETAILED DESCRIPTION OF THE INVENTION

Applicants have found that low levels of the ethylene glycol impurity, particularly about 0.05% to about 3% by weight of ethylene glycol, in commercial sodium isethionate solutions can be readily removed by a two-phase extractive process utilizing one of the following aliphatic alcohols or mixtures thereof; namely, n-propanol, isopropanol, n-butanol, 2-butanol, isobutanol and t-butanol.

It has also been discovered that the concentration of the sodium isethionate solute must be within the range of about 40% by weight dissolved sodium isethionate to the saturation level for the particular temperature selected for the extraction. This concentration range will insure that the extraction efficiency will be maximized as exemplified hereinafter. At room temperature the saturation level is about 65% by weight of dissolved sodium isethionate. Further, the relative amount of ethylene glycol extracted with a given amount of alcohol has been found to increase with increasing dissolved sodium isethionate content of the solution. However, the preferred concentration range for the dissolved sodium isethionate in solution at room temperature, is from about 50 to 65% and most preferred from about 55 to 65%.

The temperature of the extraction process is not critical and may be conducted at temperatures below room temperature, e.g. about 15° C, up to about 10° C below the boiling point of the solvent, i.e. about 10° C less than the boiling point of the particular aliphatic alcohol used as the solvent, e.g. in the case of isopropanol the temperature is about 72° C. However, to avoid excessive extraction of water and contamination of the aqueous phase with excessive amounts of the organic solvent it is preferred to operate within the limits of about 15° C to about 60° C.

The pH of the aqueous phase is also not critical to the extraction process. Commercial sodium isethionate solutions are generally finished to a pH within the range of about 8 to about 10.5 in order to precipitate any iron salts present as the hydroxides which are readily removed by filtration. Thus, pH's within the broad range from about 3 to 12 can be readily utilized. A pH range from about 6 to about 10, however, is preferred in order to avoid either corrosion problems or introduction of unnecessary amounts of electrolyte which might have an adverse effect either on subsequent coconut acyl isethionate manufacture or the properties of the detergent bars made therefrom.

Another surprising feature of the extraction process is that the three carbon alcohols, i.e. n-propanol or isopropanol which are normally miscible with water in all proportions, form two phases with the isethionate solutions within the concentration range described above. The lower alcohols, methanol and ethanol, on the other hand, which also are miscible with water in all proportions, also are miscible with the isethionate solution forming no separate liquid phase. In fact, ethanol causes extensive precipitation of the sodium isethionate when added to a 56% sodium isethionate solution. From the points of view of efficiency and economy (i.e. maximum extraction of the ethylene glycol and maximum recovery of the solvent), the three carbon alcohols are preferred, with isopropanol most preferred.

Mixtures of the three and/or four carbon aliphatic alcohols may also be utilized. This is particularly advantageous where a three and/or four carbon alcohol side stream or side product may be available within the chemical complex of the manufacturing facility. Such mixed alcohols are available at low cost and therefore are very economical to use in the instant invention.

The extraction process can be carried out either in a batch or continuous manner. The amount of alcohol that is used may range from a few percent by weight of the aqueous sodium isethionate solution to several times the given weight of the isethionate solution. Thus, the effective amount of solvent required to accomplish extraction varies widely in relation to process parameters such as temperature, concentration of sodium isethionate, type of solvent and process mode, i.e. batch or continuous. When operating in a batch mode, for reasons of economy and efficiency, it is preferred to utilize an amount of the alcohol in the range of from about 5% to about 50% and most preferred from about 10% to about 25% by weight of isethionate solution to be extracted. The manner of operation is simply to bring together the alcohol and the aqueous sodium isethionate solution into intimate contact as obtained, for example, by vigorous mixing, allowing the organic or solvent phase to separate as an upper layer, withdrawing the upper layer and then repeating the process with fresh alcohol until the level of ethylene glycol in the aqueous phase is lowered to the desired extent.

When operating in the continuous mode of extraction, which is preferred to the batch mode, the amount of alcohol utilized will depend on the design of the extraction equipment utilized. In the continuous mode, alcohol is introduced through a dispersion tube either by gravity or by forced pumping into the bottom of the extraction vessel holding the sodium isethionate solution to be extracted. Provision of an agitation zone in the mixture gives the greatest efficiency in terms of the amount of alcohol that has to be recycled. Due to the large difference in density between the alcohol and isethionate solution, the alcohol will rise rapidly and after passing through the agitation zone (if one is provided) and through suitably perforated baffles (if provided—to dampen the motion of the mixed aqueous solution/solvent phase) separates into a clear layer at the surface of the aqueous sodium isethionate solution. The upper alcohol layer is continuously withdrawn and discharged into an evaporator which distills off the volatile solvent leaving the extracted glycol impurity in the evaporator vessel. The alcohols vapors are then condensed in a suitable condenser and the distillate is returned to the extraction vessel either by gravity feed or by forced pumping through the dispersion tube in the bottom of the vessel.

The mechanical method of introducing the alcohol in the extraction vessel is not an essential feature of the invention although it can effect the efficiency of the extraction. Such mechanical arrangements are well known and will be obvious to those skilled in the solvent extraction art. One suitable dispersion tube consists of a concentric stainless steel pipe perforated with a series of holes having a diameter in the range from about 1/64 inches to ⅛ inches. A bank of connected fritted glass pipes also may serve as a suitable means of introducing the alcohol in the form of minute droplets which provide intimate contacting of the aqueous solution with the solvent and thereby enabling an efficient extraction of the glycol impurity from the aqueous phase.

A simultaneous benefit of the extraction process is the elimination of extractible color bodies which may be present in the commercial aqueous sodium isethionate solution. This feature provides for producing an even higher quality isethionate solution, namely, one that is completely water white.

Residual amounts of the extraction solvent which remain in the aqueous phase are readily removed by using, for example, one of the following methods: (a) sparging the extracted aqueous layer with either air or an inert gas under atmospheric or vacuum conditions, (b) subjecting the extracted aqueous phase to a vacuum with or without heating; for example, passing the aqueous solution through a thin-film evaporator is a suitable method of removing the organic solvent or (c) heating and distilling the aqueous phase until the vapor temperature reaches that of water, e.g. 100° C at 760 mm.

Since solvent extraction of the isethionate solutions is generally accompanied by some removal of water as well as ethylene glycol, it is usually desired to add make-up water to the extracted isethionate solution to avoid deposition of crystals of the sodium isethionate or to dissolve any solids that may have precipitated during the extraction process.

Small amounts of sodium isethionate that may be carried over with the extraction solvent can also be recovered by evaporation of the solvent followed by precipitation with acetone and filtration.

The analytical method used for determining the level of ethylene glycol in the aqueous sodium isethionate solution before and during extraction is a standard iodometric-periodic acid method. For example, the following method is satisfactory. A sample of the sodium isethionate solution (sample size depends on the ethylene glycol content: 0.5 g to 2.5 g is usually the range for a solution containing 3% down to about 0.5% or less ethylene glycol) is accurately weighed and mixed with 50 ml of 0.01 molar $HIO_4$ in 0.25 N $H_2SO_4$ and allowed to stand in the dark for 30 minutes. Then 20 ml of 15% KI solution is added and the solution stirred rapidly for at least 1 minute with a magnetic stirrer. The solution is then titrated with standard (0.1 N) sodium thiosulfate solution to the near disappearance of the brown iodine color. Two ml of a 1% starch indicator solution is then added and the titration is continued to the disappearance of the blue starch-iodine complex. A blank is also run with 50 ml of water and omitting the sample. From the titrations of the blank and test sample, the percent ethylene glycol is readily calculated. When sodium sulfite or other reducing material is also present in the sample, the ethylene glycol value must be corrected for the amount of sulfite present (i.e. calculated in terms of ethylene glycol equivalent). Sodium sulfite is readily determined by standard iodometric analysis.

The following nonlimiting examples are provided to illustrate the invention. All parts, percentages and proportions utilized herein and in the appended claims are by weight unless otherwise indicated.

EXAMPLES 1–19

Examples 1–19 illustrate the batch extraction of aqueous sodium isethionate solutions utilizing the alcohols of the invention and other solvents for comparison, under various conditions. The different procedures utilized are described in Methods A and B below. The results are tabulated in Tables I and II.

METHOD A 191.5 grams (145 cc) of an aqueous sodium isethionate solution, containing 57% by weight dissolved solids (sodium isethionate plus trace impurities) and 3.0% by weight ethylene glycol, is placed in a 200 cc Stokes flask and extracted with one or more consecutive portions of solvent as noted in Tables I and II. After each addition of the alcohol, the mixture is shaken for 3 minutes, the alcohol layer is allowed to separate and is then siphoned off. In some of the cases of the multiple extractions, a reduction in volume of up to about 10% of the original aqueous solution is noted and is due mainly to extraction of some water along with the ethylene glycol impurity. (Due to this volume reduction, the actual amount of ethylene glycol removed is slightly higher than those reported in the Examples, particularly for the three carbon alcohols).

METHOD B

The procedure utilized in Method A is repeated except 140 cc (193.2 g) of a sodium isethionate solution containing 65% by weight dissolved solids, i.e. 65% by weight of sodium isethionate and trace impurities and about 3% by weight of ethylne glycol are used in place of the 57% solution. In addition, four consecutive 35 cc portions of solvent are utilized in the extraction.

TABLE I

| Example | Solvent | % Ethylene Glycol in Aqueous Phase After Extraction | % of Original Ethylene Glycol Removed From Aqueous Phase |
|---|---|---|---|
| 1 | Isopropanol | 2.71 | 11 |
| 2[a] | Isopropanol | 2.74 | 12 |
| 3[b] | Isopropanol | 2.15 | 29 |
| 4 | n-Propanol | 2.80 | 7 |
| 5 | n-Butanol | 2.75 | 8 |
| 6 | Isobutanol | 2.78 | 7 |
| 7 | t-Butanol | 2.68 | 11 |
| 8[a] | t-Butanol | 2.82 | 9 |
| 9 | Methyl ethyl ketone | 2.99 | 0.3 |
| 10 | Butyl Cellusolve | 2.87 | 4 |

[a]Extraction temperature is 50° C.
[b]Method B utilized.

TABLE II

| Example | Solvent | % Ethylene Glycol In Aqueous Phase After final Extraction | % of Original Ethylene Glycol Removed From Aqueous Phase |
|---|---|---|---|
| 11[a] | Isopropanol | 1.61 | 46 |
| 12[b] | Isopropanol | 1.39 | 54 |
| 13 | Isopropanol | 1.51 | 50 |
| 14 | n-Propanol | 2.14 | 30 |
| 15 | n-Butanol | 2.43 | 19 |
| 16 | Isobutanol | 2.23 | 27 |
| 17 | t-Butanol | 1.83 | 39 |
| 18[c] | 2-Butanol | 2.11 | 31 |
| 19 | n-Amyl Alcohol | 2.70 | 10 |

[a]Method B and four consecutive extractions with 35 cc portions of solvent are utilized.
[b]Five 53 cc portions of solvent (each portion corresponding to about 37% of the volume of the aqueous phase) are utilized.
[c]The extraction is carried out in a 100 cc graduated cylinder utilizing 80 cc (108.0 g) of the sodium isethionate solution and five consecutive extractions with 20 cc portions of the solvent. Method is otherwise the same as A.

Comparison of the results in Tables I and II for the solvents of the invention versus the prior art amyl alcohol and two miscellaneous well-known solvents, methyl ethyl ketone and butyl cellsolve, clearly show the superior performance of the solvents of the invention.

The level of ethylene glycol in the aqueous phase in each of the above pertinent examples is readily lowered further by additional successive batch extractions or by utilizing continuous extractions as exemplified in Examples 20–22 below.

EXAMPLES 20–22

Examples 20–22 illustrates the continuous mode extraction of aqueous isethionate solutions utilizing isopropanol as the solvent.

A standard laboratory continuous liquid/liquid extraction apparatus as described in the aforementioned Weisberger reference, is employed.

In Example 21, 210 cc of a commercial aqueous sodium isethionate solution, containing about 57% dissolved solids (i.e. sodium isethionate plus trace impurities) is "spiked" with ethylene glycol to raise the ethylene glycol level from an orginal 0.44% to 3.06%. The "spiked" solution (at pH of 9.1) is placed in the cylindrical extraction vessel and continuously extracted with isopropanol at a throughput rate of about 5.6 cc/min. over a period of 6 hours. The temperature of the extraction averaged about 27° C. Samples are withdrawn periodically and analyzed for ethylene glycol:

| Hours of Extraction | % Ethylene Glycol In Aqueous Phase | % Ethylene Glycol Removed From Aqueous Phase |
|---|---|---|
| 2 | 1.38 | 55 |
| 5 | 0.81 | 74 |
| 6 | 0.63 | 79 |

EXAMPLE 21

289 g of an out-of-specification commercial aqueous sodium isethionate solution, containing about 54% dissolved solids (i.e. sodium isethionate plus trace impurities), 0.94% ethylene glycol, pale yellow in color and at a pH of 6.6 is continuously extracted at 25–27° C in the same manner as described above for Example 20 for a total of 7 hours. The results are as follows:

| Hours of Extraction | % Ethylene Glycol In Aqueous Phase | % Ethylene Glycol Removed From Aqueous Phase |
|---|---|---|
| 1 | 0.51 | 46 |
| 2 | 0.35 | 63 |
| 3 | 0.26 | 73 |
| 6 | 0.13 | 86 |
| 7 | 0.06 | 94 |

The extracted aqueous layer is now water-white—all color bodies are removed by the extraction process.

EXAMPLE 22

303 g of commercial aqueous sodium isethionate solution, containing about 56% dissolved solids (i.e.

sodium isethionate plus trace impurities), 1,90% ethylene glycol and at initial pH of 9.2 is continuously extracted at 25–27° C as described in Example 20. The results are as follows:

| Hours of Extraction | % Ethylene Glycol In Aqueous Phase | % Ethylene Glycol Removed from Aqueous Phase |
|---|---|---|
| 1 | 0.91 | 69 |
| 4 | 0.42 | 86 |

Having described the invention, persons skilled in the art will be aware of modifications not specifically set forth herein.

What is claimed is:

1. A process for the extraction of ethylene glycol impurity from an aqueous solution of sodium isethionate having dissolved therein said sodium isethionate in an amount of about 40% to about the saturation level thereof and wherein said ethylene glycol impurity is present in an amount of about 0.05% by weight to about 3% by weight comprising the steps of:

i. contacting said aqueous solution with an amount sufficient to result in said extraction of a solvent selected from the group consisting of n-propanol, isopropanol, 2-butanol, isobutanol, n-butanol and mixtures thereof at a temperature of about 15° C to a temperature of about 10° C below the boiling point of the solvent selected, wherein a solvent phase and an aqueous phase are formed, and ii. removing the solvent phase containing the extracted ethylene glycol.

2. A process as defined in claim 1 wherein the solvent is selected from the group consisting of n-propanol and isopropanol.

3. A process as defined in claim 1 wherein the solvent is isopropanol.

4. A process as defined in claim 1 wherein the extraction temperature ranges from about 15° C to about 60° C.

5. A process as defined in claim 1 wherein the sodium isethionate solution contains about 50% to about 65% of dissolved sodium isethionate.

6. A process according to claim 1 wherein said aqueous phase is further treated to remove residual solvent.

\* \* \* \* \*

UNITED STATES PATENT AND TRADEMARK OFFICE
CERTIFICATE OF CORRECTION

PATENT NO. : 4,003,925
DATED : January 18, 1977
INVENTOR(S) : Vincent Lamberti, et al It is certified that error appears in the above-identified patent and that said Letters Patent are hereby corrected as shown below:

In the Specification:

Column 2, line 41: After the word "then", add the words:
   --utilize it in the--.

Signed and Sealed this

Third Day of May 1977

[SEAL]

Attest:

RUTH C. MASON
*Attesting Officer*

C. MARSHALL DANN
*Commissioner of Patents and Trademarks*